US011117018B2

(12) United States Patent
Malis et al.

(10) Patent No.: US 11,117,018 B2
(45) Date of Patent: Sep. 14, 2021

(54) SYSTEM FOR MEASURING, MONITORING AND DISPLAYING PHYSICAL PARAMETERS OF EXERCISES ON SELECTORIZED FITNESS MACHINES

(71) Applicants: Vadim Malis, San Diego, CA (US); Oliver Kurt Karl-Heinz Ernst, San Diego, CA (US); Nelson Nientsu Hua, San Diego, CA (US)

(72) Inventors: Vadim Malis, San Diego, CA (US); Oliver Kurt Karl-Heinz Ernst, San Diego, CA (US); Nelson Nientsu Hua, San Diego, CA (US)

( * ) Notice: Subject to any disclaimer, the term of this patent is extended or adjusted under 35 U.S.C. 154(b) by 34 days.

(21) Appl. No.: 16/561,524

(22) Filed: Sep. 5, 2019

(65) Prior Publication Data

US 2020/0070001 A1 Mar. 5, 2020

Related U.S. Application Data

(60) Provisional application No. 62/727,513, filed on Sep. 5, 2018.

(51) Int. Cl.
*A63B 24/00* (2006.01)
*A63B 21/062* (2006.01)
(Continued)

(52) U.S. Cl.
CPC ........ *A63B 24/0062* (2013.01); *A61B 5/1176* (2013.01); *A63B 21/0628* (2015.10);
(Continued)

(58) Field of Classification Search
CPC ............ A63B 24/0062; A63B 21/0628; A63B 2220/30; A63B 2220/51; A63B 2220/62;
(Continued)

(56) References Cited

U.S. PATENT DOCUMENTS

| 8,062,182 B2 * | 11/2011 | Somers | ............... A63B 21/0628 482/8 |
| 2007/0213183 A1 * | 9/2007 | Menektchiev | ......... A63B 24/00 482/94 |

(Continued)

*Primary Examiner* — Nyca T Nguyen
*Assistant Examiner* — Andrew M Kobylarz
(74) *Attorney, Agent, or Firm* — Volpe Koenig

(57) ABSTRACT

A system for measuring, displaying, storing and utilizing user-specific exercise data from selectorized fitness machines, including the weight, repetitions, and any other physical parameters derivable from the weight and displacement of the weight stack. The system is comprised of two coupled sensor systems: an infrared sensor and multiple Hall effect sensors. The sensors are mounted to an adjustable stand that can be retrofitted to any selectorized fitness machine. The system analyzes the measurements and sends the data to a server for storage on a per-user basis. Users are identified by a near-field communication (NFC) tag or facial recognition. The system uses an innovative coupled NFC/QR/facial recognition—Bluetooth paradigm to transmit exercise data in real-time to the Bluetooth-enabled mobile device of the user. A mobile application allows users to view the exercise data, to follow predefined workout plan, and to retrieve stored data from a remote server.

15 Claims, 13 Drawing Sheets

(51) Int. Cl.
*A61B 5/1171* (2016.01)
*G01R 33/07* (2006.01)

(52) U.S. Cl.
CPC .......... *G01R 33/07* (2013.01); *A63B 2220/30* (2013.01); *A63B 2220/51* (2013.01); *A63B 2220/62* (2013.01); *A63B 2220/89* (2013.01); *A63B 2225/54* (2013.01)

(58) Field of Classification Search
CPC ............ A63B 2220/89; A63B 2225/54; A61B 5/1176; G01R 33/07
See application file for complete search history.

(56) References Cited

U.S. PATENT DOCUMENTS

| | | | |
|---|---|---|---|
| 2010/0075816 A1* | 3/2010 | Anderson | A63B 21/0728 482/107 |
| 2017/0246507 A1* | 8/2017 | Kennington | A63B 23/1209 |
| 2018/0345080 A1* | 12/2018 | Orfield | A63B 24/0075 |

* cited by examiner

SYSTEM FOR MEASURING, MONITORING AND DISPLAYING PHYSICAL PARAMETERS OF EXERCISES ON SELECTORIZED FITNESS MACHINES

CROSS REFERENCE TO RELATED APPLICATION

This application claims the benefit of U.S. Provisional Application No. 62/727,513, filed on Sep. 5, 2018, which is incorporated by reference as if fully set forth.

FIELD OF INVENTION

The present invention relates to measuring, displaying, storing and utilizing user-specific exercise data on selectorized fitness machines.

BACKGROUND

An increasingly important part of exercising is the ability to track statistics over time across workouts, gyms and machines. This includes the weight lifted, the repetition count, and other physical statistics such as the force exerted over time, the power exerted over time, energy consumed, as well as other metadata such as the machine type used, the muscle groups exercised, the exercise duration and the geographic location of the exercise.

In many commercial gyms, devices that record data about exercises are dominantly limited to cardiovascular machines, such as treadmills. Few devices are currently featured in gyms that track data for weight machines, such as weight benches, cable bicep/tricep bars, chest press machines, rowing machines, and others.

A primary difficulty in designing such devices is that the device must be able to measure data from different machines that have diverse configurations of weights and range of motions performed. Many of the existing devices which have been designed are limited to very specific machine configurations.

A second difficulty is to design a system for identifying users, displaying exercise data in real-time and storing data for later retrieval by users that is easily accessible to users, but robust across gyms and machine types. This difficulty is also shared by fitness tracking devices currently installed in gyms, where data is rarely stored permanently in the cloud for users to retrieve and analyze later.

It would be advantageous to have a device that addresses these challenges for selectorized fitness machines such as will now be described by the present teachings in greater detail.

SUMMARY

The present invention discloses a system for measuring, monitoring and displaying physical statistics resulting from exercises on selectorized fitness machines. Hall effect sensors, either omnipolar or bipolar, are attached to an adjustable vertical stand, independent of the fitness machine. Magnets are placed on each weight plate of the weight stack of the fitness machine in alternating North/South orientations. The Hall effect sensors are oriented such that they are able to register the magnetic field resulting from these magnets. An infrared sensor is mounted to the same stand as the Hall effect sensors, measuring the displacement and speed of the lifted part of the weight stack during an exercise. A computing module is attached to the device, which features a near-field communication (NFC) antenna or a camera. When a user logs in to the device using an NFC tag or using facial recognition via the camera, a Bluetooth connection is automatically established between the computing device and the Bluetooth-enabled smartphone of the user. This allows exercise data to be transmitted in real-time to the user.

A primary object of the present invention is a device which can measure the weight lifted, count the repetitions performed in real time, and measure any physical statistics that can be derived from the combination of the weight measurement and the displacement over time of the weight stack, including but not limited to: energy consumption, force exertion, power exertion, duration of repetitions, time in-between repetitions, and others.

Another object of the present invention is the adjustability of this device to fit any existing selectorized fitness machine installed in any home or commercial gym, with no permanent modifications to the machine.

Another object of the present invention is a communication paradigm between a computing module attached to a fitness machine and the Bluetooth-enabled smartphone of a user based on the NFC(QR)/Face Recognition—Bluetooth paradigm. The data may be stored, visualized and analyzed using a smartphone application. This paradigm used in the context of fitness machines enables exercise regiments that can be remotely monitored by a fitness trainer. This paradigm also enables the collection of metadata for commercial gym that monitors the popularity, effectiveness and fatigue of fitness machines.

Additional features and components of the invention will be described in the Detailed Description that follows.

DETAILED DESCRIPTION OF THE PREFERRED EMBODIMENTS

To fully describe the invention, a detailed description will now follow, with reference to the drawings FIG. 1 through FIG. 10. These drawings represent an example of what the invention may entail. The present invention may be embodied in other forms but featuring the same essential characteristics. The scope of the invention is precisely defined by the appended claims.

A selectorized fitness machine is defined by a stack of weight plates, hereby referred to as a weight stack, which move in a vertical motion, supported by poles running vertically through the plates. The motion of the machine by the user is translated into vertical motion of the weight stack by a cable or a belt, where the weight lifted is adjustable by a pin or lever. These machines are broadly featured in commercial and home gyms, and are used to train many diverse muscle groups.

The present invention relates to measuring, displaying and storing user-specific exercise data of exercises performed on selectorized fitness machines. The invention includes the sensors necessary for such measurements, the adjustable sensor array stand that may be attached to any existing selectorized fitness machine, and the necessary algorithms to extract further statistics from these measurements. A second innovation of the present invention is the use a coupled NFC(QR)/Face Recognition—Bluetooth paradigm to transmit exercise data in real-time from a computer system attached to a fitness machine to the Bluetooth-enabled mobile device of the user.

Figure 1:
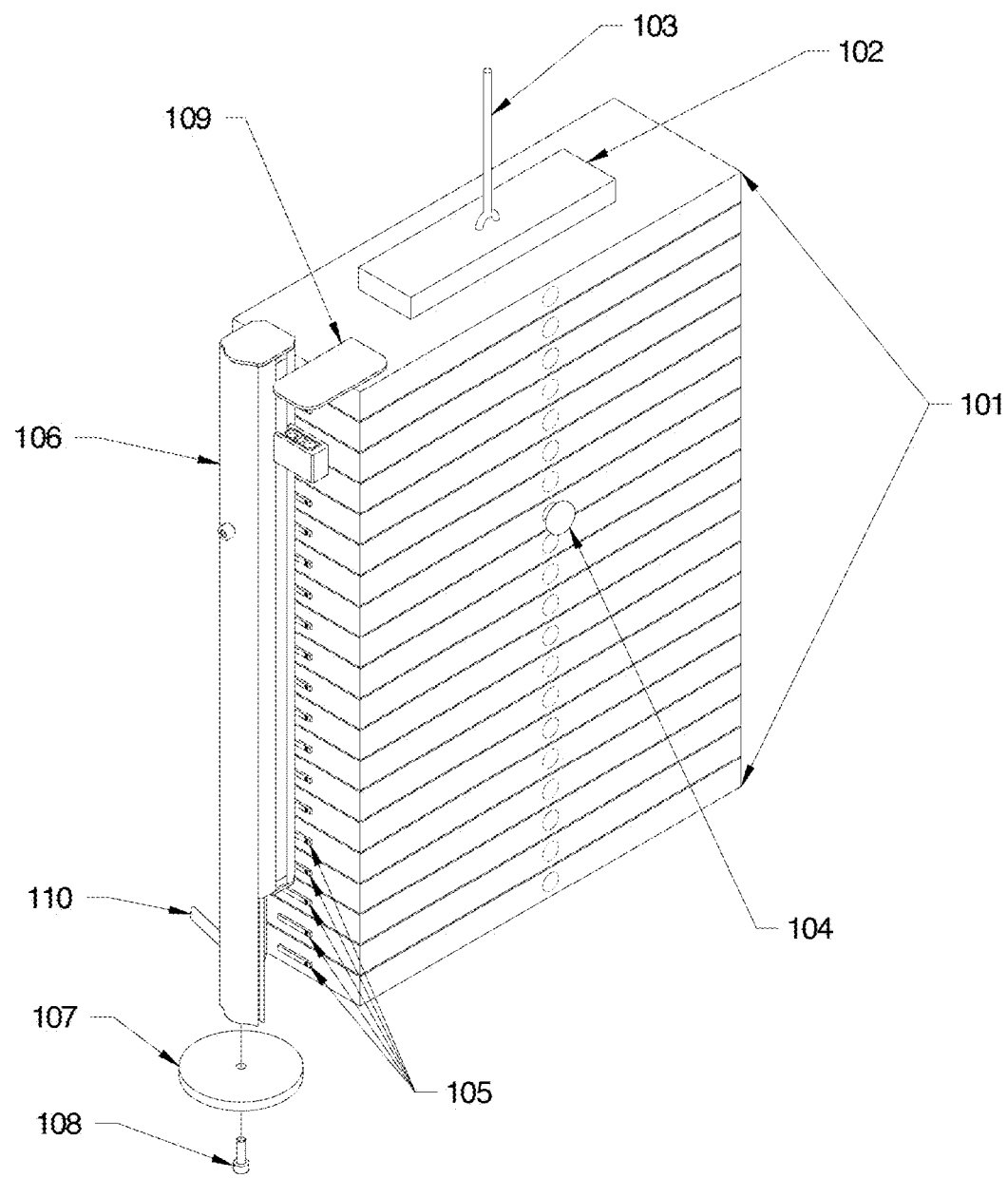
FIG. 1 is a perspective view of the device of the present disclosure installed on a weight stack of a selectorized fitness machine.

Referring now primarily to FIG. 1, which illustrates the setup of the device to record data from the weight stack 101 of a selectorized fitness machine. A typical weight stack such as this one includes a selector rod 102 attached to the cable 103 and a pin 104 for weight selection. For the device to function, a magnet is attached to each plate of the weight stack 105, with alternating polarities on sequential weight plates to maximize the heterogeneity of the magnetic field. A standalone sensor stand with adjustable height 106 is placed to any side of the weight stack 101 facing the magnets 105. The sensor stand 106 can be attached to the fitness machine frame either by a mounting screw 107, a magnet 108, vise, or just placed nearby on a floor with the base pad attached. A reflector 109 is magnetically attached to the top weight plate of a weight stack 101. The sensor stand is connected by communication cable 110, such as an Ethernet type 8-channel cable, to a computing device, which analyzes the measurements as described further and demonstrated in FIG. 3.

Figure 2:
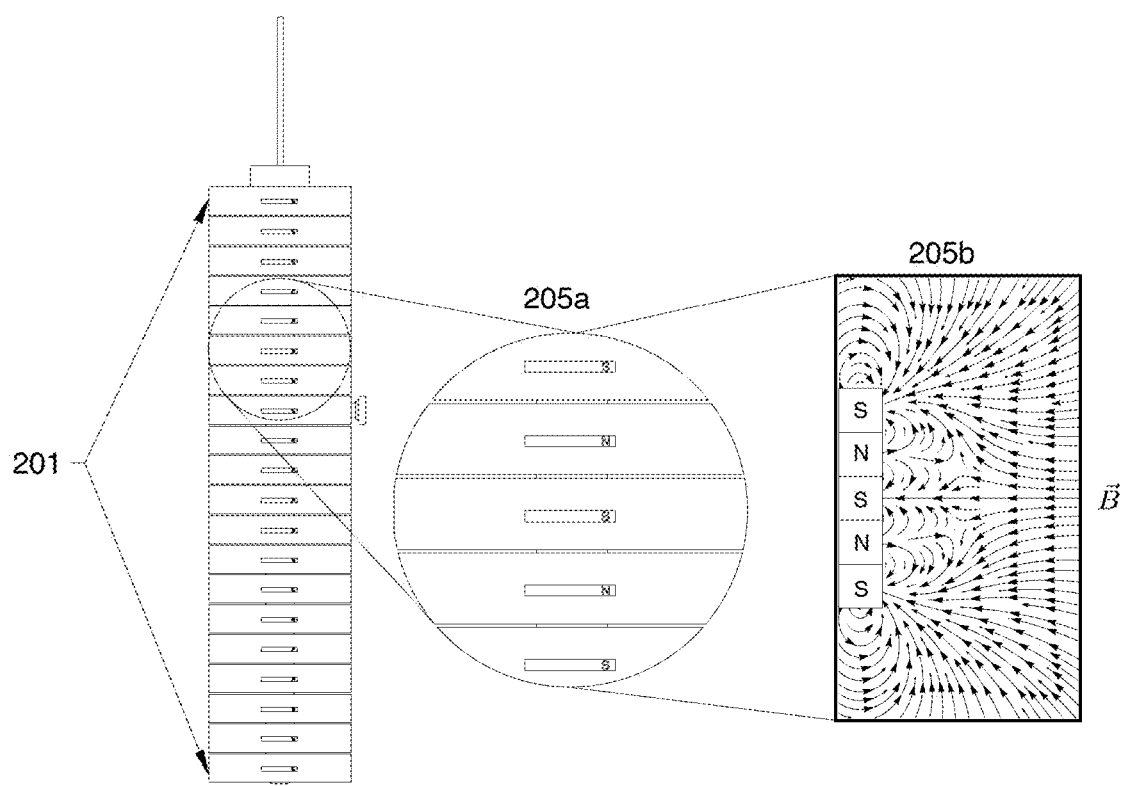
FIG. 2 is a side view of FIG. 1 with an enlarged view of the heterogeneous magnetic field produced by the alternating orientations of the magnets.

Referring now primarily to FIG. 2, which illustrates the magnet arrangement 105 from FIG. 1. The magnets of neighboring weight plates of weight stack 201 alternate their magnetic poles on the side facing the sensor stand. The magnet arrangement 205a creates pronounced alternating magnetic field lines 205b, making it possible to resolve the field of an individual plate by a bipolar Hall effect sensor.

Figure 3:
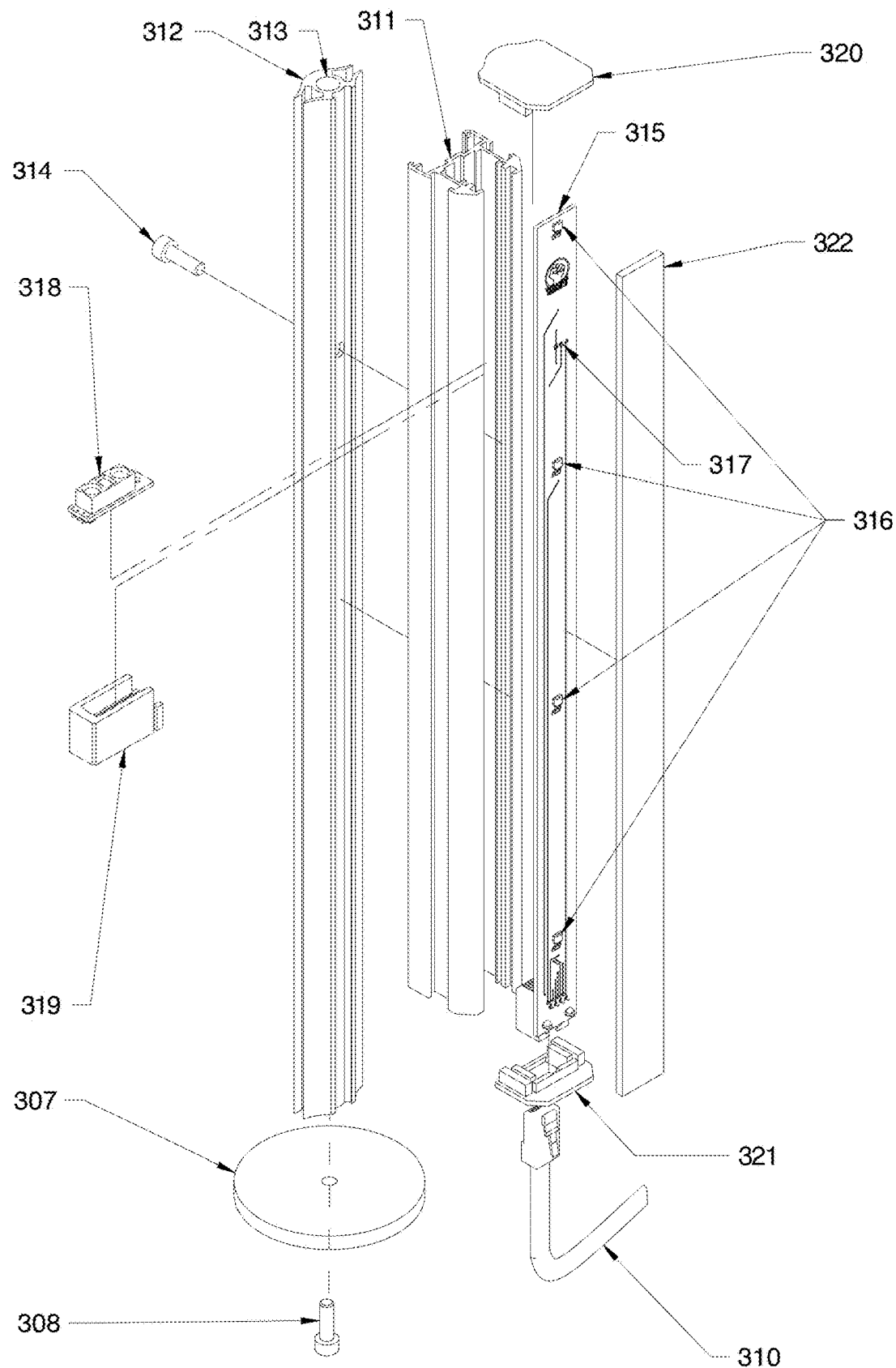
FIG. 3 is an exploded view of the sensor stand.

Referring now primarily to FIG. 3, which illustrates the key components of the sensor stand 106. A profile 311 is capable of sliding along another fixed profile 312, which may be made of aluminum in one embodiment, or other suitable materials such as plastic. To enable the stand to stand on its own, a mounting magnet or base pad 307 and a screw 308 are attached to the fixed profile 312 from the bottom through mounting hole 313. The height of the sliding profile 311 can be adjusted with stop screw 314. Printed circuit board (PCB) 315 is inserted into the slot of the sliding profile 311. This PCB 315 features several evenly spaced bipolar Hall effect sensors 316, and a connection to a displacement sensor 317. The displacement sensor 318, which in one embodiment may be an infrared sensor, is embedded into an adjustable-height holder 319 and can be attached to either side of the sliding profile 311 and sealed with a plastic cap 320 from the top and stub end 321 from the bottom. A communication cable 310, such as an Ethernet type 8-channel cable, is plugged into the PCB 315 through the stub 321. A plastic cover 322 is inserted into slots of the sliding PCB 311 to protect the exposed side of the PCB featuring the Hall effect sensors.

Figures 4A, 4B:
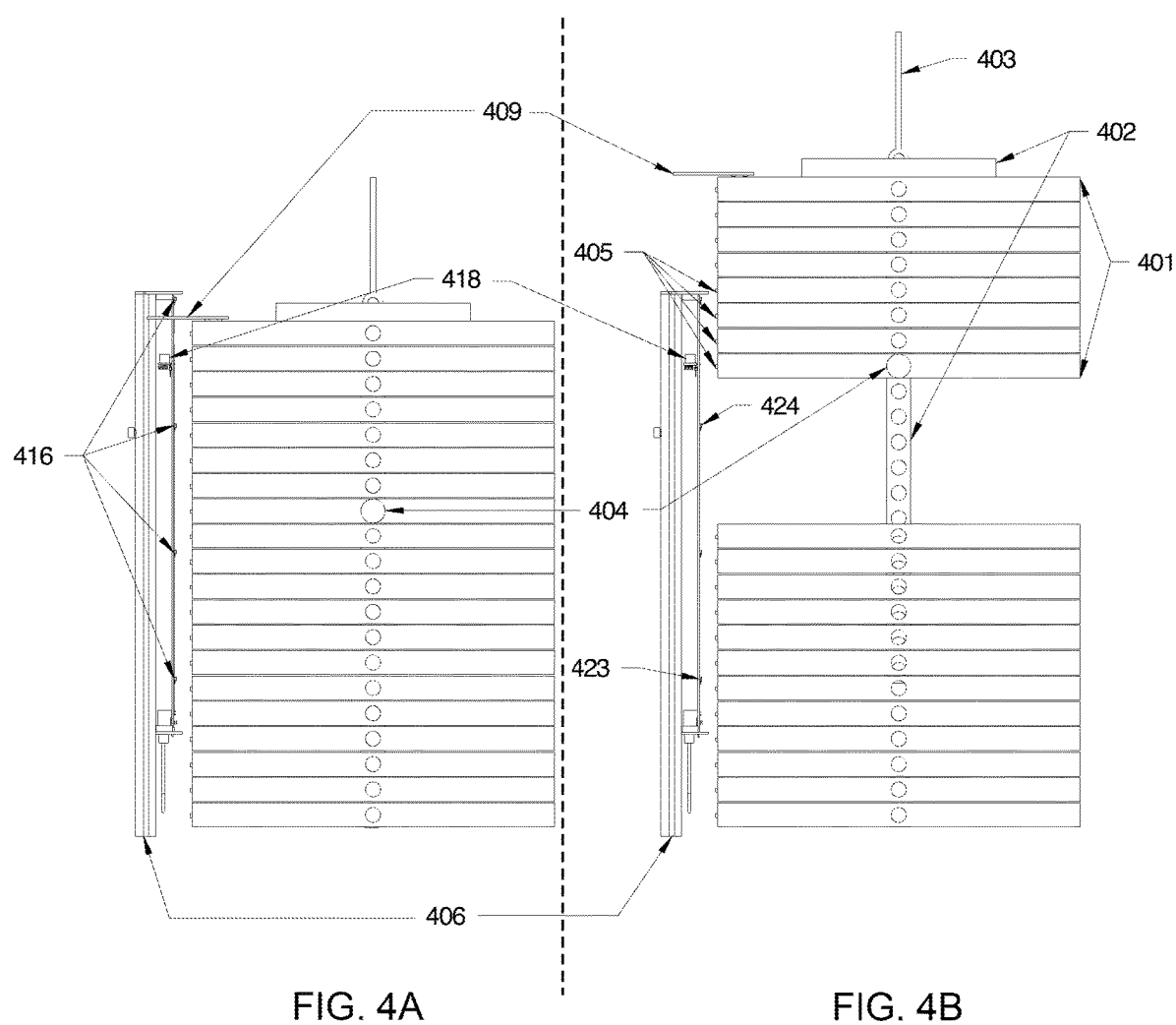
FIG. 4A is a side view of the device and weight stack when the weight stack is in an idle position.
FIG. 4B is a side view of the device and weight stack during an exercise.

Referring now primarily to FIG. 4A, which illustrates the initial position of the weight stack at the idle position. The sensor stand 406 with bipolar Hall effect sensors 416 is located in front of the weight stack. During an exercise (FIG. 4B) weight plates 401 locked to the selector rod 402 via the weight selecting pin 404 are pulled up by the cable 403. The displacement sensor 418 is making continuous measurements of the distance to the reflector 409. Once the displacement from the idle position is greater than the separation between Hall effect sensor, the lowest activated Hall effect sensor 424 is identified and the count of the number of magnets 405 that passed the lowest sensor 424 is used to calculate the lifted weight. The displacement sensor 418 continues to measure displacement throughout the entire duration of the exercise. Weight calculations are repeated once the weight stack returns to the idle position and stays in the idle position for a pre-determined timeout interval, which is the least amount of time necessary for weight selection.

Figure 5:
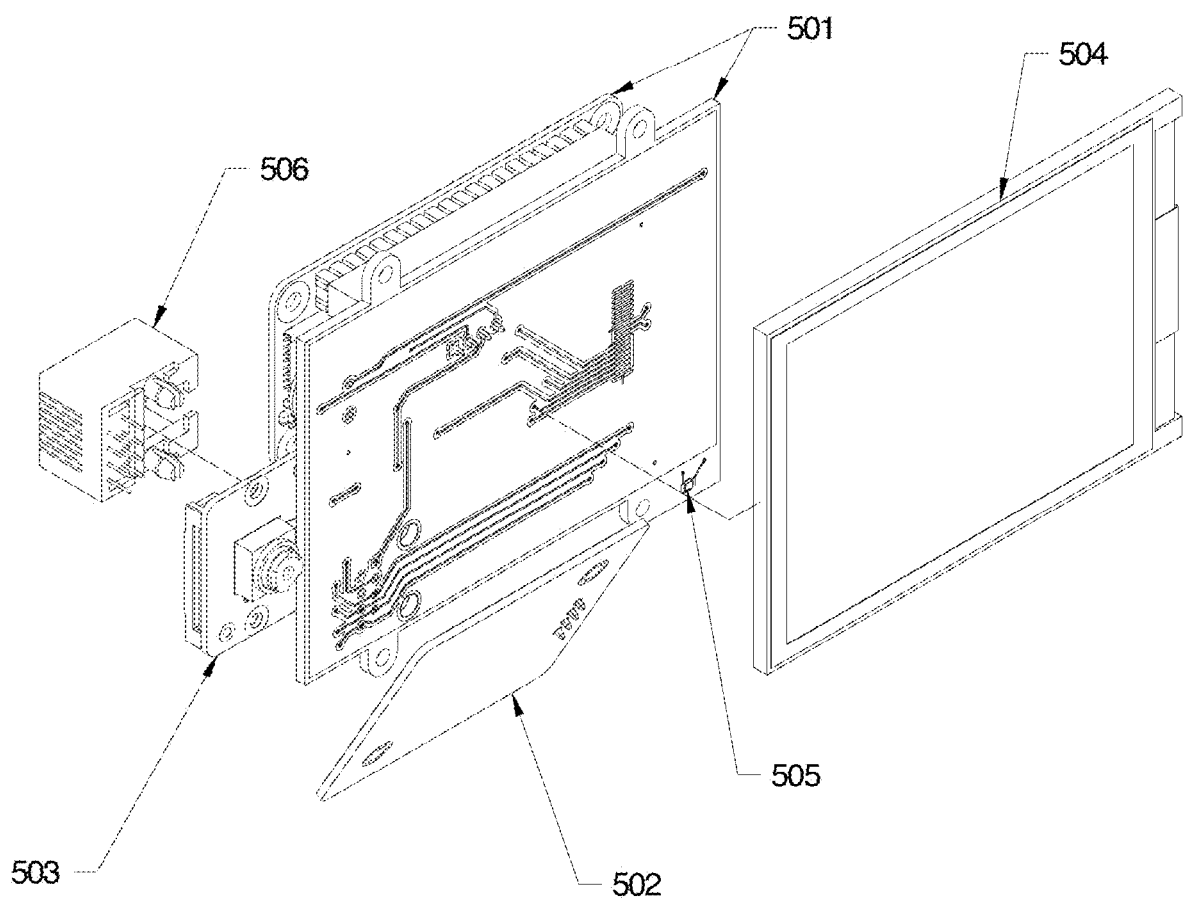
FIG. 5 is an exploded view of the computing module and associated hardware.

Referring now primarily to FIG. 5, which illustrates the key components of the computation device. The computing module 501 is equipped with Bluetooth Low Energy (BLE), Wi-Fi interface, Near Field Communication (NFC) antenna 502 or in another embodiment a camera 503, color LCD screen 504, piezoelectric buzzer, an LED indicator light 505, a plug for communication cable 506 and a power supply.

Real-time workout information can be displayed on the computing device. The device can be mounted to the protective cover surrounding the weight stack on many fitness machines, or otherwise to the fitness machine frame.

Figure 6:
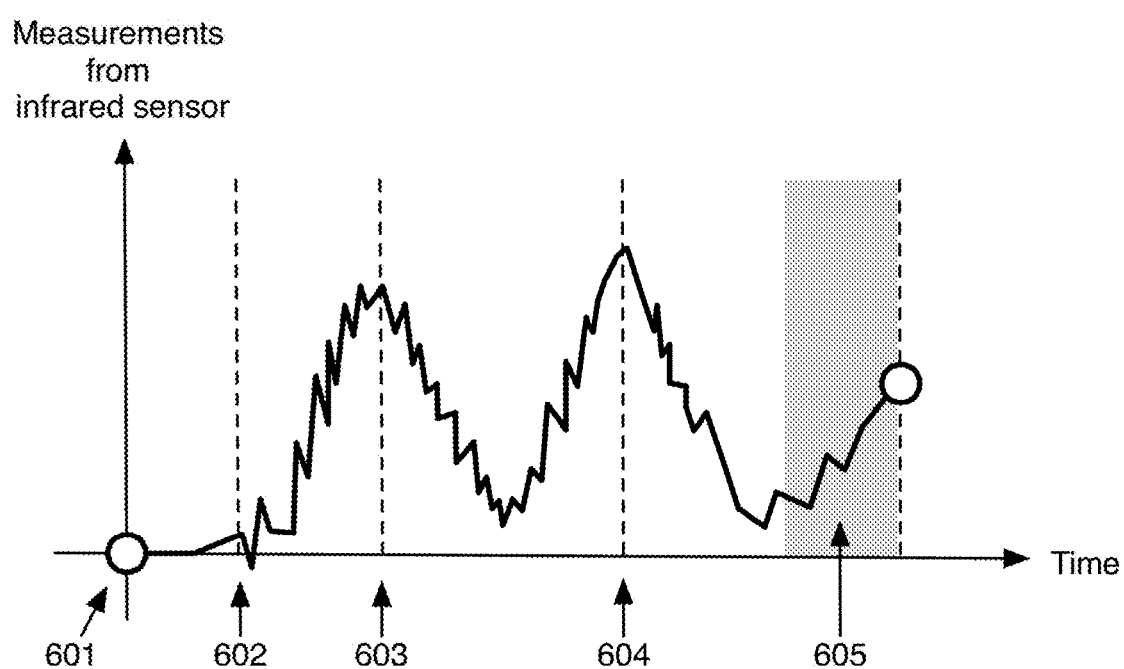
FIG. 6 is an example graph of raw measurements obtained by the infrared sensor and the relation in time to exercise events.

Referring now primarily to FIG. 6, which depicts an example of what the measurements made by the infrared sensor may look like, both before and during the exercise. The example process begins with a user logging in to the device at time 601. The user begins the exercise at time 602. The weight stack reaches the peak height for the first time at time 603, as computed from the measurements of the infrared sensor. The weight stack reaches a peak height for a second time at time 604. These peak times are determined by analyzing a window 605 of the most recent measurement data from the infrared sensor, which is used to determine whether the weight stack has reached a maximum height during this window.

Figure 7A:
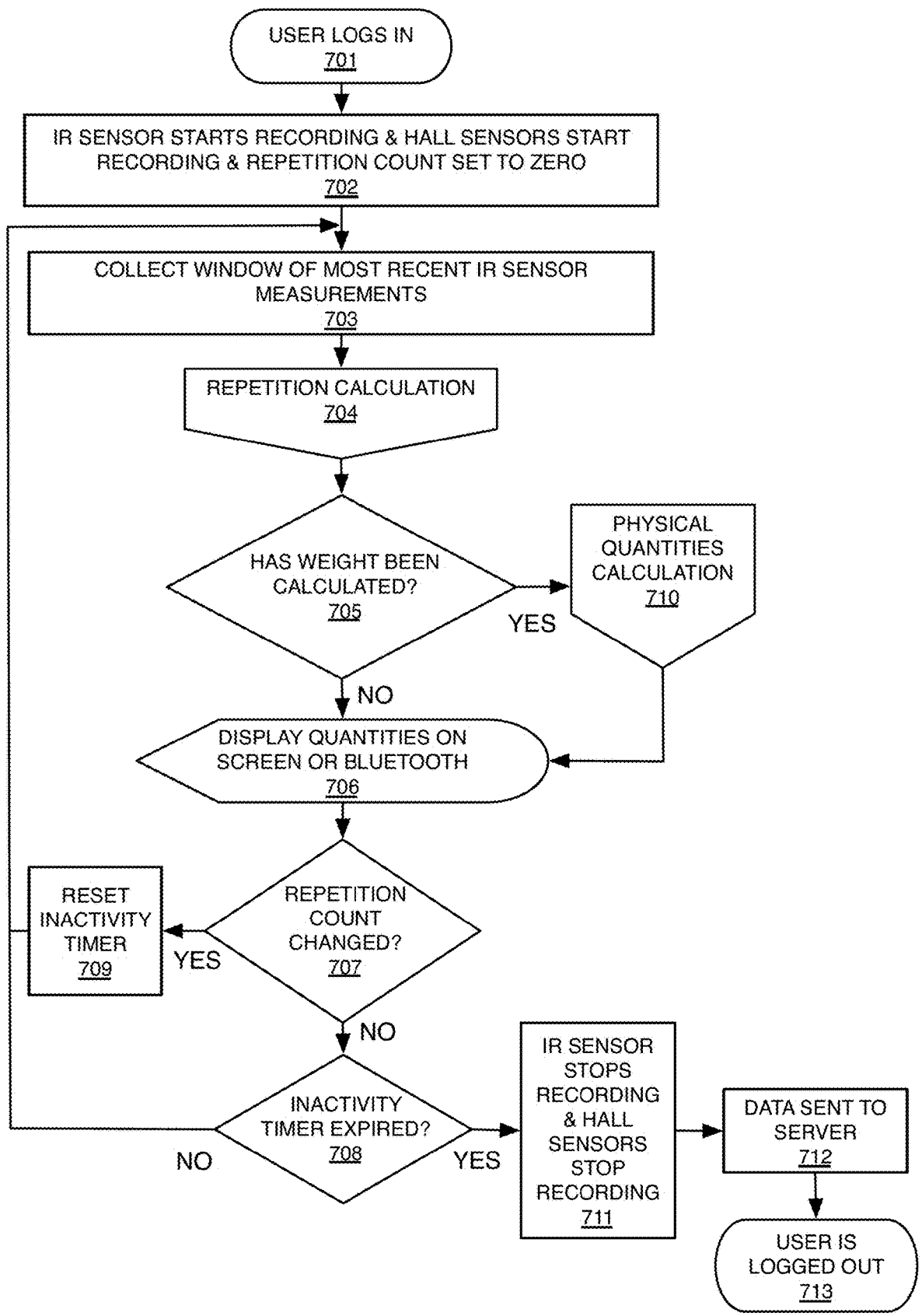
FIGS. 7A-7D are flowcharts for determining the weight, repetition count, and other physical quantities associated with an exercise and for displaying such physical quantities to a user.

Referring now primarily to FIG. 7A, which depicts a diagrammatic view of the usage of the device by a user under normal operating conditions. The user logs into the device 701, at which time the Hall sensors and infrared sensor will start recording, and the initial repetition count will be set to zero 702. The device collects the most recent measurement data from the infrared sensor into a window of a certain size 703, which is analyzed to determine whether the user has performed an exercise repetition 704. If the weight has been previously calculated 705, further physical quantities may be computed asynchronously 710 from the displacement and weight data. The new calculated quantities are displayed 706, either on a screen, or on the mobile device of the user which is connected by Bluetooth. If the repetition count has changed during this time window 706, this reflects that the user is actively using the machine, and any inactivity timer is reset 709. In this case, a new window of data is collected, and the steps 703, 704, 705, 710, 706 are repeated. If the repetition count has not changed during this time window 707, inactivity timer is checked 708. If the inactivity timer has not expired, a new window of data is collected, and the steps 703, 704, 705, 710, 706 are repeated. If the inactivity timer has expired, the logout process is triggered 711, and the user is logged out 713.

Figure 7B:
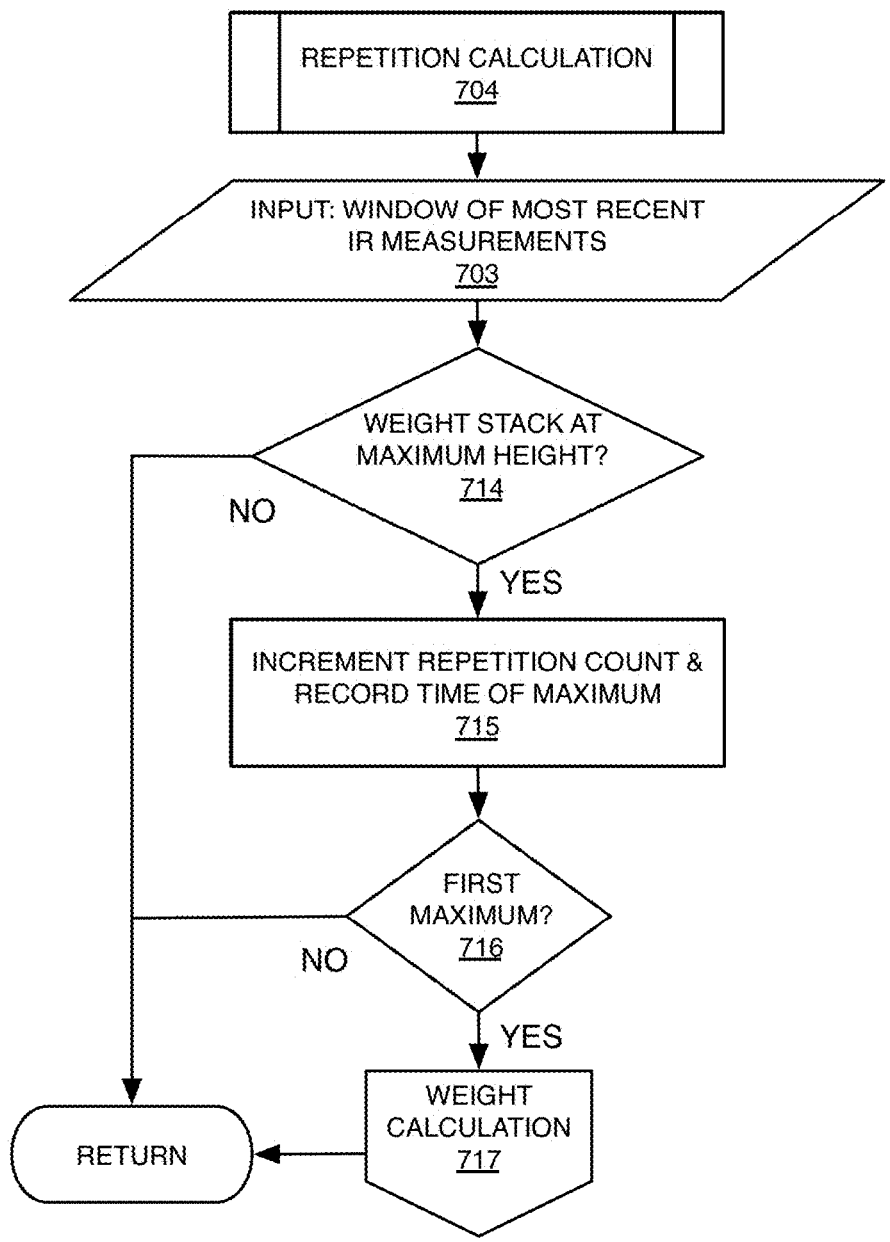
Figure 7C:
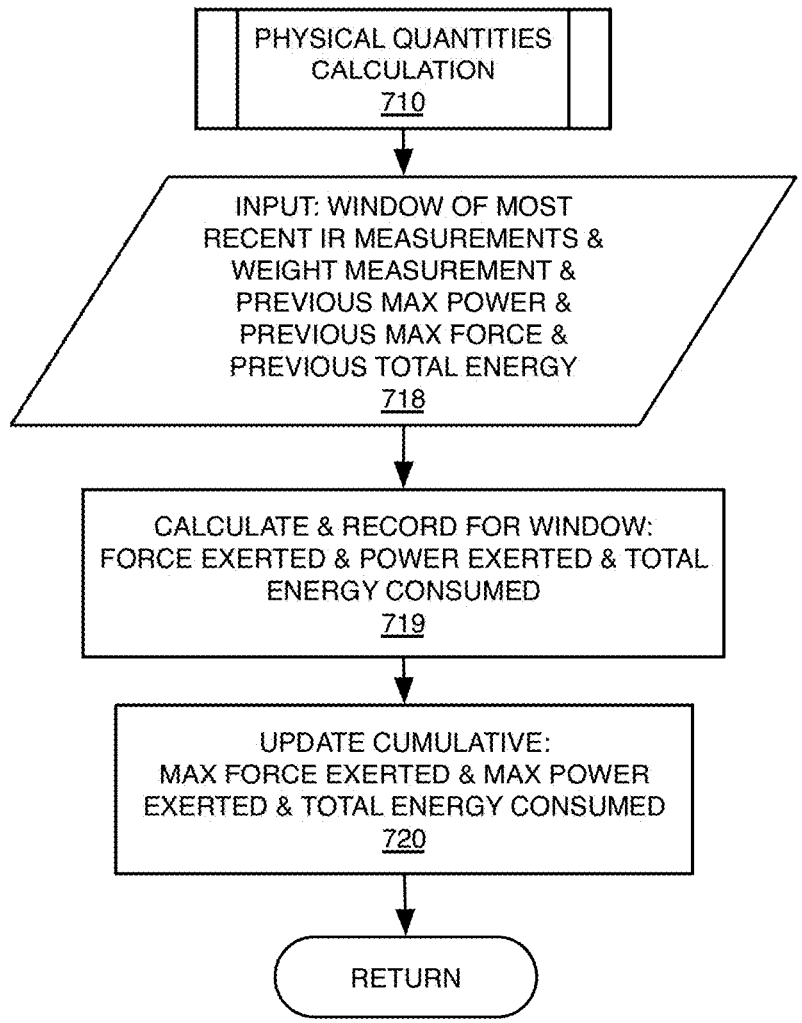

Referring now primarily to FIG. 7B, which depicts a diagrammatic view of the data analysis procedure 704 applied to the window of measurements made by the infrared sensor 703 and Hall sensors. If a peak is detected in the window 714, the repetition count is incremented 715. If it additionally is the first peak for the user's exercise 716, the weight is calculated 717 from the combination of the infrared measurements and Hall sensor recordings. FIG. 7C depicts a diagrammatic view of the calculation 710 of further physical quantities associated with the exercise. These are derived from the combination of the displacement measurements made by the infrared sensor and the measurement of the weight 718. From these measurements, quantities such as the force and power exerted at all times during the time window may be derived, and the total energy consumed during the window 719. Statistics over the whole exercise may be tracked 720, such as the maximum force and power exerted, and the total energy consumed during the exercise.

Figure 7D:
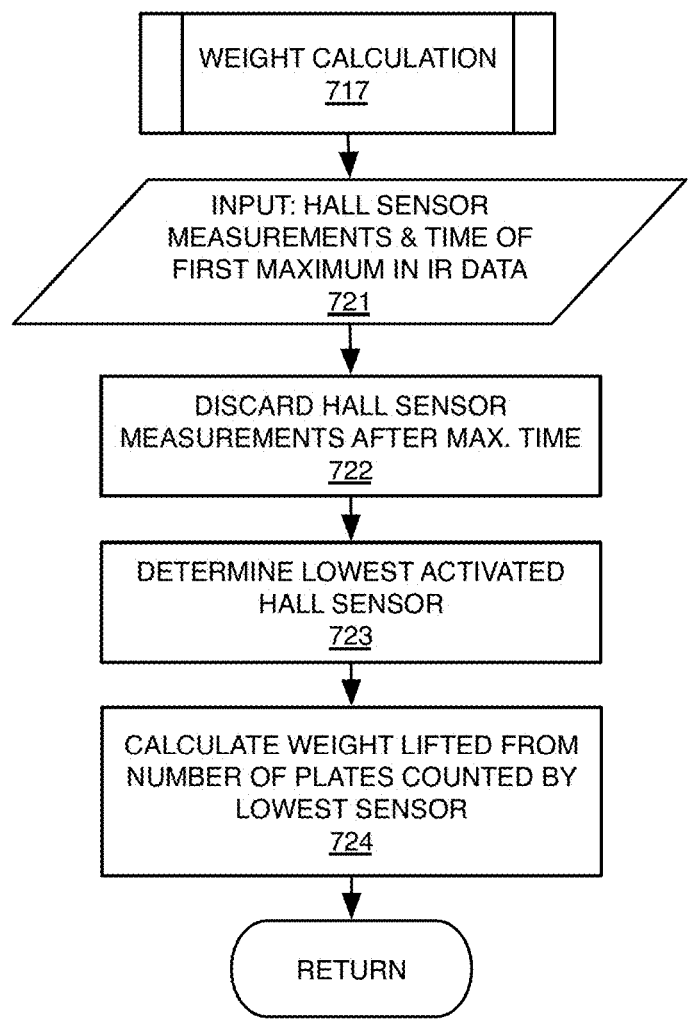

Referring now primarily to FIG. 7D, which depicts a diagrammatic view of the weight calculation 717 from the combination of the Hall sensor measurements and the peak times calculated from the infrared sensor measurements 721. Hall sensor measurements recorded after the time of the first peak are discarded 722. Only the data collected by the lowest Hall sensor 723 is required to count the number of plates that have been lifted. From this, the weight is calculated by multiplying the count by the corresponding weight of each plate 724.

Referring now primarily to FIG. 7E, which depicts a diagrammatic view of the logout process 711. If a Bluetooth mobile device is paired to the device 725, a signal is sent from the device to the application on the mobile device to disconnect 726. After both devices disconnect, the device stops advertising the Bluetooth service 727. The infrared sensor and Hall sensors stop recording 728. Exercise data is sent to the server 729 and the user is logged out 713.

Figure 8A:
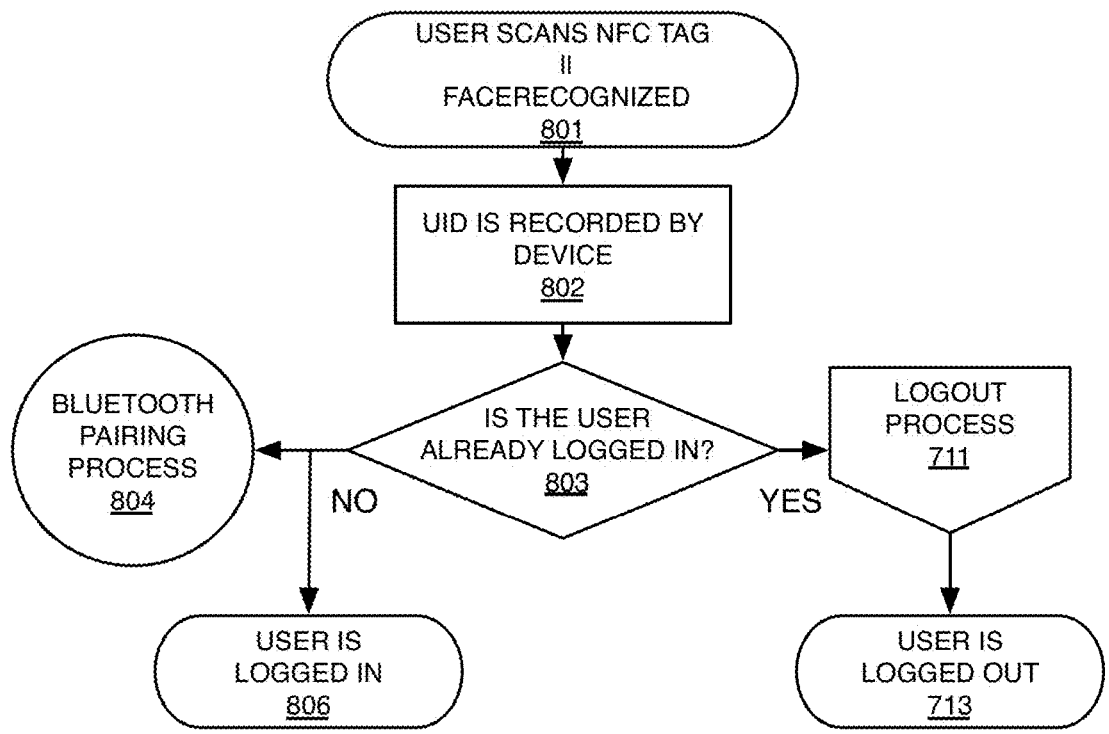
FIGS. 8A and 8B are flowcharts for connecting and disconnecting the device to a mobile device of a user.

Referring now primarily to FIG. 8A, which depicts a diagrammatic view of the login by a user into the device using the NFC&QR/Face Recognition—Bluetooth paradigm. In one embodiment a user scans their NFC tag 801, from which a unique ID (UID) is recorded by the device 802. In another embodiment, a user's face is detected by a camera from which a user's UID is determined by device 802. If the user is not logged in 803, the user is logged in 806, and the process to pair the device to the mobile device starts asynchronously 804. If the user is already logged in 803, the logout process is triggered 711, and the user is logged out 713.

Figure 8B:
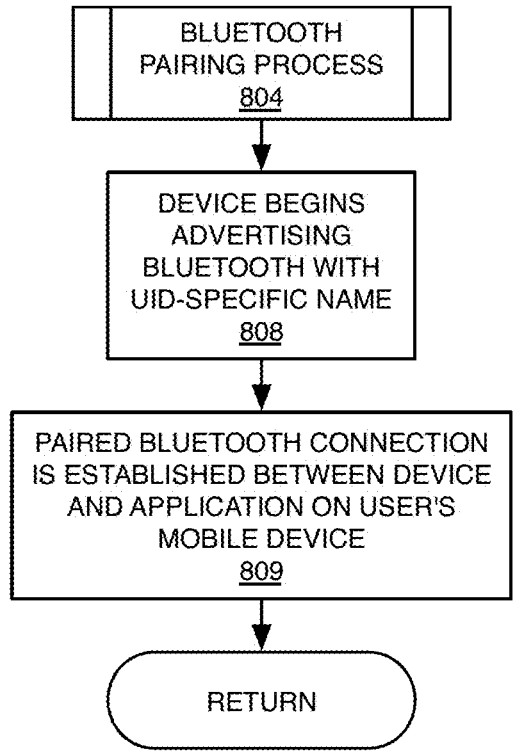

Referring now primarily to FIG. 8B, which depicts a diagrammatic view of the Bluetooth pairing process 804. The device advertises a Bluetooth service with a name specific to the UID obtained during log in process (FIG. 8A). The application on the mobile device searches for this Bluetooth service, thereby completing the pairing process 809.

Figure 9:
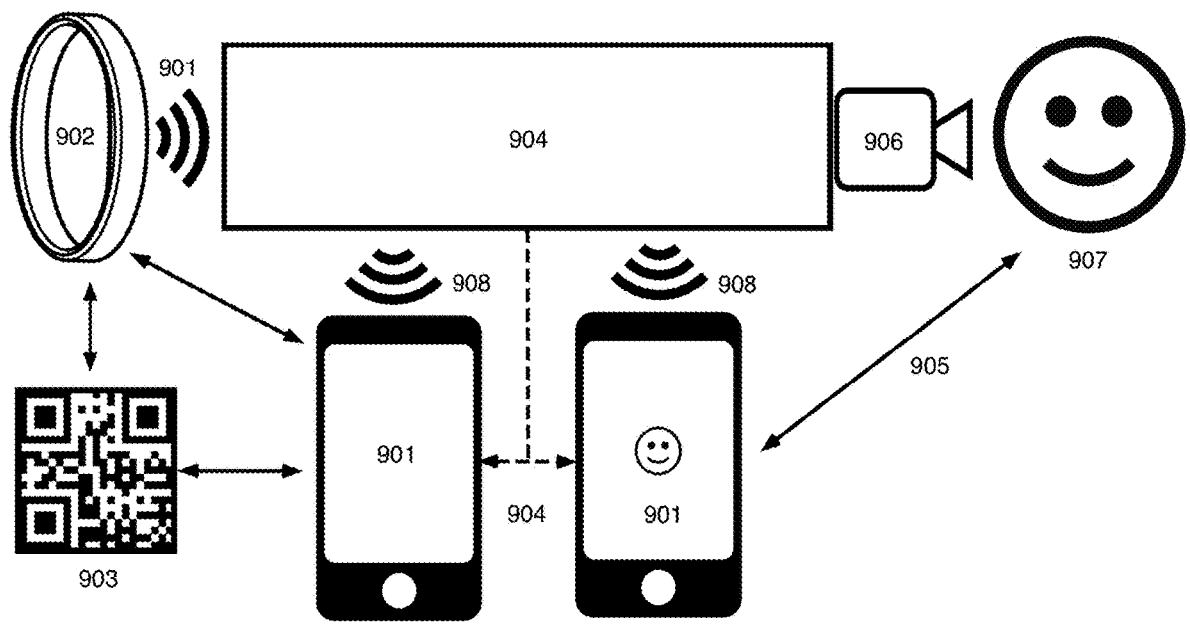
FIG. 9 is a diagram illustrating interactions between the identification (e.g. NFC(QR)/Face) device and the mobile device of the user.

Referring now primarily to FIG. 9, which depicts the usage of the device by user employing the NFC&QR/Face Recognition—Bluetooth paradigm. The Bluetooth-enabled smartphone 901 of the user is associated to a corresponding NFC tag 902. In one embodiment, this NFC tag may be an existing tag embedded in the smartphone 901. In another embodiment, this NFC tag may be a wristband 902, which is associated with the smartphone of the user, for example by scanning a QR code 903 on the smartphone. After the NFC tag has been associated with the smartphone, the user can log in to the device 904 by scanning the NFC tag against the NFC antenna on the device. In another embodiment, user's face is associated with the smartphone through the mobile app 905. User can log in to device 904 using camera 906 for Face Recognition 907. The log in process automatically prompts the device 904 to establish a Bluetooth connection 906 to the smartphone 901 of the user. When exercise data is ready to be displayed, it can then be transmitted 908 in real-time from the device 904 to the smartphone 901 to display and store the data.

The system can be retrofitted to any selectorized fitness machine without permanent modifications to the machine. This means that a gym that wants to make its machines digital does not have to buy entirely new machines—they simply install the device of the present teachings, and it becomes digital.

The device of the present teachings is stand-alone. The only parts that are moving are the magnets. This has the following advantages:

Limiting moving parts avoids wear and extends the lifetime of the device.

The machine can be used normally (without this device), where (1) the user does not see any modifications, and (2) there is no extra resistance to the motion of the machine.

The NFC-Bluetooth implementation (or similar embodiments) means that users can see the data in real-time without needing to pair manually. Simply walk up, scan your wristband or be identified with camera and your phone automatically shows in real-time the data.

Figure 10:
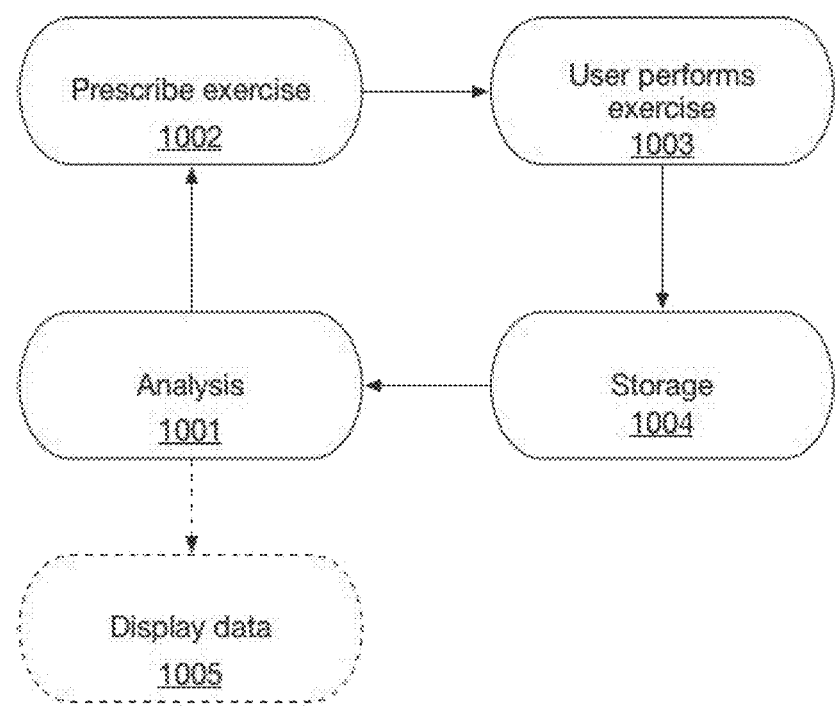
FIG. 10 illustrates a scheme of utilizing the collected data for generating personalized fitness plans.

A novel and unique prescribed exercise system with the procedure illustrated by FIG. 10, which in one embodiment maybe a "virtual trainer", which can customize a user's exercise routine for personalized fitness, such as to lose weight, gain muscle bulk, tone flabby musculature, improve flexibility, improve cardiovascular endurance and literally any other fitness goals a user may have. In one embodiment, the virtual trainer (coach) can be on a mobile device (e.g., cellular telephone) application, operatively coupled to the system of the present teachings, and analyzes prior activity 1001 by the user, and prescribes a new set of exercises to the user 1002. After the user performs the exercise 1003, the data is stored 1004, and sent back to the coach for further iterative analysis 1001. The results of the analysis are shown to the user 1005.

In one embodiment, a prescribed exercise system is enabled by the disclosed present teachings. In this embodiment, a user can virtually interact with a coach over a distance using a mobile device, wherein the coach can prescribe an exercise for a user. In this embodiment, the coach can monitor various parameters of the user's exercises, such as the energy burned, force expended, etc.

The coach can prescribe new exercises based on, inter alia, a user's performance. In one variation of the aforementioned embodiment, a coach can be replaced by a machine learning algorithm, which may learn from the history of what coaches have prescribed as exercises for various users, as well as other physical parameters associated with the user such as age and weight, and can prescribe new exercises for a user based on these data.

Another major advantage of the present teachings is the assembly requires low financial investment to build. For example, Hall sensors, magnets, and infrared sensors are low cost, inexpensive to manufacture and do not require ongoing maintenance. Moreover, there is a low probability of failure, due to the highly reliable specifications of the required components.

Several devices that record exercise data of exercise machines have been devised. Additionally, paradigms for storing user exercise data on remote servers have been developed. For example, devices for counting repetitions of an exercise and devices for calculating the weight listed by a user during an exercise have previously been disclosed. However, these devices are incapable of calculating other exercise parameters such as force, energy, power, etc. Further, these devices may not be retrofitted to any selectorized fitness machine, and instead must be custom made for the machine. In addition, these devices are not designed to be communicatively coupled to a user's mobile device via NFC, facial recognition, and/or Bluetooth technologies.

What is claimed is:

1. A system comprising:
   a plurality of magnets, each magnet attached to a weight plate of a plurality of weight plates comprising a weight stack, wherein the magnets attached to adjacent weight plates have alternating polarities moving up the weight stack;
   a plurality of Hall effect sensors mounted on a stand positioned adjacent to the weight stack, the plurality of Hall effect sensors being oriented to measure a magnetic field of the plurality of magnets, wherein the plurality of Hall effect sensors detects a number of weight plates lifted during an exercise, wherein there are less Hall effect sensors than magnets, the plurality of Hall effect sensors; and
   at least one displacement sensor mounted on the stand, the at least one displacement sensor configured to detect a displacement of the weight plates lifted during an exercise.

2. The system of claim 1, wherein the plurality of Hall effect sensors and the at least one displacement sensor are communicatively coupled to a computing module.

3. The system of claim 2, wherein the computing module comprises a near-field communication (NFC) antenna or a camera.

4. The system of claim 3, wherein the computing module is configured to identify a user based on a unique identification tag associated with an NFC tag or a face of the user.

5. The system of claim 4, wherein the computing module is configured to establish a Bluetooth connection with a mobile device of the user upon scanning of the NFC tag or recognition of the face of the user.

6. The system of claim 5, wherein, the computing module is configured to automatically transmit exercise data in real-time from the computing module to the mobile device of the user upon establishment of the Bluetooth connection.

7. The system of claim 2, wherein the computing module is configured to collect metadata of a plurality of exercises performed by a single user, the metadata including a muscle group exercised, a duration of an exercise and a time between exercise repetitions for each exercise of the plurality of exercises.

8. The system of claim 1, wherein the at least one displacement sensor is further configured to detect a speed of the weight plates lifted during the exercise.

9. The system of claim 8, wherein measurements collected from the plurality of Hall effect sensors and the at least one displacement sensor are used to determine one or more of energy consumption, force exertion, power exertion, duration of repetitions, or time in-between repetitions.

10. The system of claim 1, further comprising a reflector attached to a top plate of the weight stack, wherein the displacement sensor uses the reflector as a reference point to measure displacement.

11. The system of claim 1, wherein the system is removably installed on an existing selectorized fitness machine.

12. The system of claim 1, wherein the plurality of Hall effect sensors are omnipolar sensors or bipolar sensors.

13. A method of installing a system, the method comprising:
    attaching a magnet of a plurality of magnets to each weight plate of a plurality of weight plates comprising a weight stack, wherein the magnets attached to adjacent weight plates have alternating polarities moving up the weight stack;
    mounting a plurality of Hall effect sensors to a stand; wherein there are less Hall effect sensors than magnets;
    positioning the stand adjacent to the weight stack such that the plurality of Hall effect sensors are oriented to measure a magnetic field of the plurality of magnets; and
    mounting at least one displacement sensor to the stand.

14. The method of claim 13, further comprising communicatively coupling the plurality of Hall effect sensors and the at least one displacement sensor to a computing module.

15. The method of claim 13, wherein the method is performed on an existing selectorized fitness machine.

* * * * *